US00PP12284P2

(12) United States Plant Patent
Verwer

(10) Patent No.: US PP12,284 P2
(45) Date of Patent: Dec. 18, 2001

(54) DAHLIA PLANT NAMED 'GALLERY MONET'

(75) Inventor: Aad Verwer, Lisse (NL)

(73) Assignee: Gebr. Verwer, Lisse (NL)

( * ) Notice: Subject to any disclaimer, the term of this patent is extended or adjusted under 35 U.S.C. 154(b) by 0 days.

(21) Appl. No.: 09/318,498

(22) Filed: May 25, 1999

(51) Int. Cl.[7] ..... A01H 5/00

(52) U.S. Cl. ..... Plt./321

(58) Field of Search ..... Plt./321

(56) References Cited

PUBLICATIONS

GTITM UPOVROM Citation for 'Gallery Monet' as per QZ PBR 980184; Feb. 11, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Dahlia plant named 'Gallery Monet', characterized by its upright, somewhat outwardly spreading and rounded plant habit; freely branching, full and dense plants; decorative inflorescence form; pink and white bi-colored ray florets with yellow towards the base; and good garden performance.

2 Drawing Sheets

BACKGROUND OF THE INVENTION

The present Invention relates to a new and distinct cultivar of Dahlia plant, botanically known as *Dahlia hybrida* and hereinafter referred to by the name 'Gallery Monet'.

The new Dahlia is a product of a planned breeding program conducted by the Inventor in Lisse, The Netherlands. The objective of the breeding program is to create Dahlia cultivars with freely branching growth habit, decorative inflorescence form, attractive ray floret colors, and good inflorescence longevity. The Gallery Dahlias are the products of cross-pollinations between unidentified selections of *Dahlia coccinea* and compact Dahlia hybrids.

The new Dahlia originated from a cross made by the Inventor of the Dahlia 'Gallery Art Deco', disclosed in U.S. Plant Pat. No. 10,525, as the female, or seed, parent with the proprietary Dahlia selection identified as VLE 6 as the male, or pollen, parent. The new Dahlia was discovered and selected by the Inventor as a single flowering plant within the progeny of the stated cross grown in a controlled environment in Lisse, The Netherlands, in 1995. The selection of this plant was based on its decorative inflorescence form and attractive ray floret coloration.

Asexual reproduction of the new Dahlia by cuttings was first conducted in Lisse, The Netherlands in 1996. Asexual reproduction by cuttings has shown that the unique features of this new Dahlia are stable and reproduced true to type in successive generations.

SUMMARY OF THE INVENTION

The cultivar 'Gallery Monet' has not been observed under all possible environmental conditions. The phenotype may vary somewhat with variations in environment such as temperature, daylength, light intensity, water and nutritional status without, however, any variance in genotype.

The following traits have been repeatedly observed and are determined to be the unique characteristics of 'Gallery Monet'. These characteristics in combination distinguish 'Gallery Monet' as a new and distinct Dahlia:

1. Upright, somewhat outwardly spreading and rounded plant habit.

2. Freely branching, full and dense plants.

3. Decorative inflorescence form.

4. Pink and white bi-colored ray florets with yellow towards the base.

5. Good garden performance.

Compared to plants of the female parent, the cultivar 'Gallery Art Deco', plants of the new Dahlia are shorter and differ in ray floret coloration.

Compared to plants of the male parent, the proprietary selection VLE 6, plants of the new Dahlia are shorter and differ in inflorescence form and ray floret coloration.

Plants of the new Dahlia are easily distinguished from plants of its sibling, the cultivar 'Gallery Cobra', disclosed in U.S. Plant patent application Ser. No. 09/338,010, in ray floret coloration as plants of the new Dahlia have pink and white bi-colored ray florets whereas plants of the cultivar 'Gallery Cobra' have orange-colored ray florets.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph on the first sheet comprises a side perspective view of a typical flowering plant of 'Gallery Monet'.

The photograph on the second sheet comprises a close-up view of typical inflorescences of 'Gallery Monet'.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer and early autumn of 1997 in Lisse, The Netherlands, in an outdoor nursery and under conditions which approximate those generally used in commercial production. During the production of the plants, day temperatures ranged between 15 and 23° C. and night temperatures ranged between 10 and 15° C. Plants were pinched one time. Measurements and numerical values represent averages of typical flowering plants about 60 to 65 days after planting into the field nursery.

Botanical classification: *Dahlia hybrida* cultivar 'Gallery Monet'.

Parentage:

*Female, or seed, parent.*—*Dahlia hybrida* cultivar 'Gallery Art Deco', disclosed in U.S. Plant Pat. No. 10,525.

*Male, or pollen, parent.*—Proprietary *Dahlia hybrida* selection identified as VLE 6, not patented.

Propagation:

*Type.*—Cuttings.

*Time to initiate roots.*—About five days with soil temperatures of 20° C.

*Time to develop roots.*—About 14 to 17 days with soil temperatures of 20° C.

*Root description.*—Fibrous and well-branched.

*Tuber description.*—Shape: Fusiform. Clump diameter: About 12 cm. Color: Close to 199C.

Plant description:

*Appearance.*—Herbaceous flowering container or garden plant. Inverted triangle; stems mostly upright and somewhat outwardly spreading giving a rounded appearance to the plant. Freely branching, about 10 lateral branches develop after removal of terminal apex (pinching); dense and full plants.

*Crop time.*—About 2 months from planting are required to produce flowering finished plants.

*Plant height.*—About 25 cm.

*Plant width.*—About 25 cm.

*Lateral branches (peduncles).*—Angle: Erect. Strength: Strong. Length: About 17 cm. Diameter: About 3 cm. Texture: Smooth, glabrous. Color: Close to 144A.

*Foliage description.*—Arrangement: Leaves opposite; leaves may be single or compound with three or five leaflets. Typically about 5 to 6 pairs of leaves per lateral stem. Shape: Ovate. Apex: Acuminate. Base: Cordate. Margin: Serrate to dentate. Length: Compound leaves with three leaflets: About 8 cm. Compound leaves with five leaflets: About 12 cm. Single leaves: About 5 cm. Width: Compound leaves with three leaflets: About 7 cm. Compound leaves with five leaflets: About 10 cm. Single leaves: About 2.5 cm. Texture: Smooth, glabrous. Color: Young foliage upper surface: 147A. Young foliage lower surface: 148B. Mature foliage upper surface: 147A; venation, 148B. Mature foliage lower surface: Close to 147B; venation, 194B. Petiole length: Compound leaves with three or five leaflets: About 4 cm. Single leaves: About 3.5 cm. Petiole color: 148A.

Inflorescence description:

*Appearance.*—Terminal inflorescences held above the foliage on strong peduncles. Decorative inflorescence form with elongated oblong to narrowly ovate-shaped ray florets; ray florets arranged acropetally on a capitulum. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 15 days in an outdoor environment; and as cut flowers, inflorescences maintain good color and substance for about 6 days in an indoor environment.

*Quantity of inflorescences.*—One per lateral shoot.

*Inflorescence bud.* Shape: Globular. Length: About 1.5 cm. Diameter: About 1.5 cm. Color: 153D.

*Inflorescences.*—Shape, in profile: Hemispherical. Diameter: About 10.5 cm. Depth (height): About 4 cm. Disc diameter: About 1.6 cm.

*Ray florets.*—Shape: Elongated-oblong to narrowly ovate. Orientation: Initially upright, outer florets perpendicular to peduncle to reflexed. Apex: Acute to cuspidate. Base: Attenuate; short corolla tube. Margin: Entire. Aspect: Straight, concave. Length: About 4 cm. Width: About 1.8 cm. Texture: Smooth, glabrous; satiny. Number of ray florets per inflorescence: About 12 to 15 rows with about 9 ray florets per row. Color: When opening: 70A. Fully opened, upper surface: Towards base, 2B; mid-section, white, 155A; towards apex, 70A to 75D to paler than 75D; fading to white, 155C, with subsequent development. Fully opened, lower surface: Mostly white, 155A; towards apex, 75A.

*Disc florets.*—Number of disc florets per inflorescence: About 30. Shape: Tubular, elongated. Apex: Five-pointed. Length: About 1.3 cm. Width: About 2 mm. Color: Immature: 70A. Mature: 75D.

*Phyllaries.*—Quantity: One whorl of 6 or 7 phyllaries. Shape: Ovate. Apex: Acute. Margin: Entire. Length: About 8 mm. Width: About 1.5 mm. Texture: Smooth, dull. Color: Upper surface: 146B. Lower surface: 146A.

*Reproductive organs.*—Androecium: Present on disc florets only. Stamen quantity: Three to five per floret. Anther color: Close to 149D. Pollen amount: Scarce. Pollen color: 8C. Gynoecium: Present on ray and disc florets. Pistil quantity: Three to five per floret. Stigma color: 17C. Style length: About 2 mm. Style color: 154B.

*Seeds.*—Seed production has not been observed.

Disease resistance: Resistance to pathogens common to Dahlias has not been observed on plants grown under commercial greenhouse or outdoor conditions.

Weather tolerance: Plants of the new Dahlia have been observed to be wind and rain-tolerant. Plants of the new Dahlia tolerant temperatures from 1° C. to 40° C., although plants are not considered winter-hardy in The Netherlands.

It is claimed:

1. A new and distinct cultivar of Dahlia plant named 'Gallery Monet', as illustrated and described.

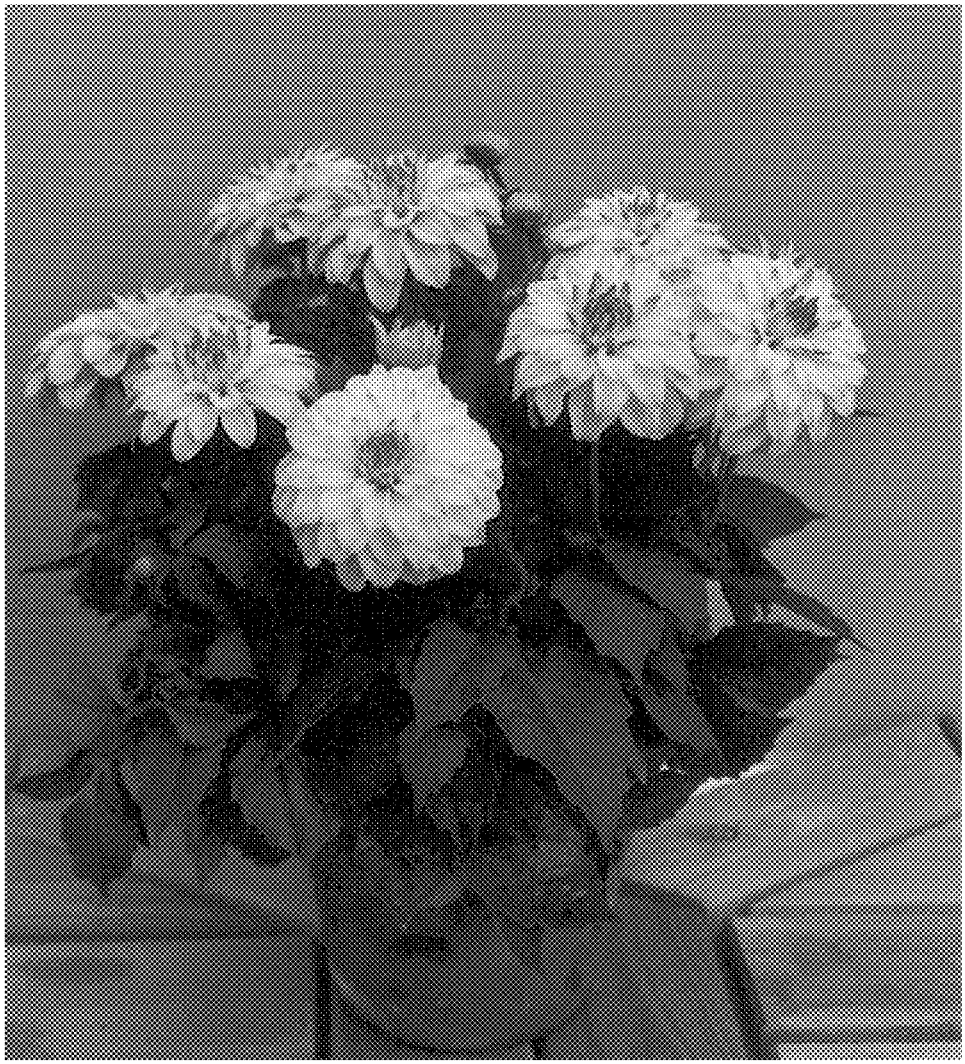

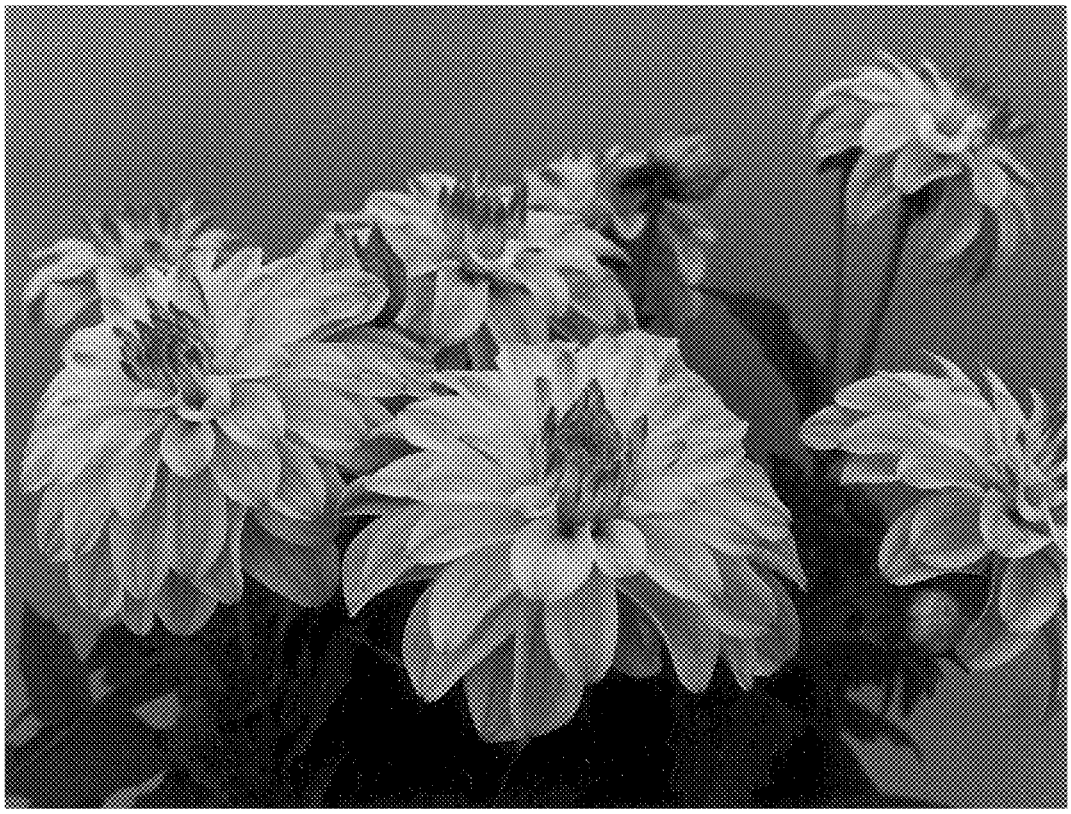

* * * * *